US008366759B2

(12) United States Patent
Dunshee et al.

(10) Patent No.: US 8,366,759 B2
(45) Date of Patent: Feb. 5, 2013

(54) THERAPY DEVICE

(75) Inventors: Wayne K. Dunshee, Maplewood, MN (US); Jessica L. Petersen, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 375 days.

(21) Appl. No.: 12/810,399

(22) PCT Filed: Dec. 23, 2008

(86) PCT No.: PCT/US2008/088200
§ 371 (c)(1),
(2), (4) Date: Jun. 24, 2010

(87) PCT Pub. No.: WO2009/086399
PCT Pub. Date: Jul. 9, 2009

(65) Prior Publication Data
US 2010/0274333 A1    Oct. 28, 2010

Related U.S. Application Data

(60) Provisional application No. 61/017,289, filed on Dec. 28, 2007.

(51) Int. Cl.
*A61F 7/00* (2006.01)
*F25D 3/00* (2006.01)
(52) U.S. Cl. .................................. 607/114; 62/530
(58) Field of Classification Search .................. 607/114; 62/530
See application file for complete search history.

(56) References Cited

U.S. PATENT DOCUMENTS

| | | | |
|---|---|---|---|
| 3,463,161 A | 8/1969 | Andrassy |
| 3,545,230 A | 12/1970 | Morse |
| 3,780,537 A | 12/1973 | Spencer |
| 3,874,504 A | 4/1975 | Verakas |
| 4,026,818 A | 5/1977 | Ciaudelli |
| 4,055,188 A | 10/1977 | Pelton |
| 4,092,982 A | 6/1978 | Salem |
| 4,462,224 A | 7/1984 | Dunshee |
| 4,596,250 A | 6/1986 | Beisang, III |
| 4,671,267 A | 6/1987 | Stout |
| 4,694,829 A | 9/1987 | Frye |
| 4,756,311 A | 7/1988 | Francis, Jr. |
| 4,770,245 A | 9/1988 | Sydansk |
| 4,854,012 A | 8/1989 | Graf |
| 4,865,012 A | 9/1989 | Kelley |
| 4,910,978 A | 3/1990 | Gordon |
| 4,953,550 A | 9/1990 | Dunshee |
| 5,150,707 A | 9/1992 | Anderson |
| 5,415,624 A | 5/1995 | Williams |
| 5,478,988 A | 12/1995 | Hughes |
| 5,513,629 A | 5/1996 | Johnson |
| 5,545,199 A | 8/1996 | Hudson |
| 5,697,961 A | 12/1997 | Kiamil |
| 5,843,145 A | 12/1998 | Brink |
| 6,017,606 A | 1/2000 | Sage |
| 6,217,606 B1 | 4/2001 | Portnoy |
| 6,241,711 B1 | 6/2001 | Weissberg |
| 6,524,612 B2 | 2/2003 | Misumi |
| 6,592,889 B1 | 7/2003 | Stout |
| 6,610,084 B1 | 8/2003 | Torres |
| 2003/0167681 A1 | 9/2003 | Delgado Puche |
| 2005/0231014 A1 | 10/2005 | Carlisle |
| 2006/0159734 A1 | 7/2006 | Shudo |
| 2007/0239238 A1 | 10/2007 | Nausid |

FOREIGN PATENT DOCUMENTS

| | | |
|---|---|---|
| EP | 1053726 | 11/2000 |
| EP | 1264585 | 12/2002 |
| WO | WO 02/087700 | 11/2002 |
| WO | WO 2007/108235 | 9/2007 |

OTHER PUBLICATIONS

Yang et al. "Value-added uses for crude glycerol-a byproduct of biodiesel production" Biotechnology for Biofuels, 2012, 5:13, p. 1-10.*
"$^{31}$P NMR Investigation of a Ringing Gel Phase and Adjacent Phases", Abstract, ingentaconnect, [available on the internet Dec. 7, 2007, retrieved from the internet on Aug. 18, 2011], <http://www.ingentaconnect.com/content/els/09277765/1996/00000007/00000005/art01296> 1 page.
Bonnardeaux, Glycerin Overview, Department of Agriculture and Food, pp. 1-13, (Nov. 2006).
Characterization of Crude Glycerol From Biodiesel Production From Multiple Feedstocks, Biodiesel Tech, vol. 3, Issue 3, 2 pages, (Fall 2006).
"Elastogel.biz Hot Cold Therapy Wraps", [viewed on the internet on Oct. 15, 2007, printed from the internet on Aug. 18, 2011], <http://web6.ehost-services.com/webmaster/elastogel/index.htm>, 2 pages.
"Glycerin Purification", [retrieved from the internet on Dec. 28, 2007], <http://ww.eetcorp.com/heepm/glycerine.htm>, 1 page.
"Glycerol", Highbeam™ Encyclopedia, The Columbia Encyclopedia, Sixth Edition, 2007, 1 page, [retrieved from the internet on Oct. 16, 2007], URL <http://www.encyclopedia.com/printable.aspx?id=1E1:glycerol>.
"ringing gel formulation", [available on the internet Dec. 7, 2007], <http://tur.proz.com/kudoz/993784>, 1 page.
Yong, Refining of Crude Glycerine Recovered From Glycerol Residue by Simple Vacuum Distillation, Journal of Oil Palm Research, vol. 13, No. 2, pp. 39-44, (Dec. 2001).
European Search Report for PCT/US2008/088200, 7 pages.
Search Report for PCT/US2008/088200, 3 pages.

*Primary Examiner* — Kortney L Klinkel
(74) *Attorney, Agent, or Firm* — Lisa P. Fulton; Kevin W. Weber

(57) ABSTRACT

A therapy device comprises a flexible sealed envelope and a gel within the envelope. The gel comprises water, thickening agent, and biodiesel by-product glycerin comprising glycerol and soap.

21 Claims, No Drawings

THERAPY DEVICE

CROSS REFERENCE TO RELATED APPLICATIONS

This application is a national stage filing under 35 U.S.C. 371 of PCT/US 2008/088200, filed Dec. 23, 2008, which claims priority to Provisional Application No. 61/017289, filed Dec. 28, 2007, the disclosure of which is incorporated by reference in its/their entirety herein.

FIELD

This invention relates to a therapy device comprising a thermal gel that can be used as a hot or cold compress.

BACKGROUND

The treatment of many injuries such as sprains, contusions, or dislocations where immediate swelling is common typically involves application of cold ice compresses or other materials to slow the flow of blood to the injured site, thus reducing swelling. After the initial trauma and swelling due to the injury have subsided, however, it is often advisable to apply heat to the injured area to promote healing. Here again, a number of expedients have been used in the past for this purpose, including hot towels or heating pads.

Therapy devices comprising a sealed envelope with a material inside that can be used for application as desired of either heat or cold (that is, the material functions as a heat source or heat sink, respectively) have been used or at least known for some time. In some embodiments, the devices are for one time use; in other embodiments the devices can be reused, for example, following heating by immersion in hot water or irradiation in a microwave oven or cooling by placement in a cooler, freezer, etc. Some illustrative examples of such therapy devices are disclosed in U.S. Pat. No. 3,780,537 (Spencer), U.S. Pat. No. 3,874,504 (Verakas), U.S. Pat. No. 4,462,224 (Dunshee), U.S. Pat. No. 4,854,012 (Kelley), U.S. Pat. No. 5,697,961 (Kiamil), and U.S. Pat. No. 5,843,145 (Brink).

A number of heat source/sink materials have been suggested for use in therapy devices. Among the desired performance criteria are that the material exhibit a desirable degree of conformability throughout the useful temperature range so that it can be conformed to the injury location to provide effective therapeutic treatment. One commonly used gel that is currently frequently used in hot/cold compresses is petroleum-based propylene glycol. Though well performing, this material is derived from petroleum and thus does not come from a sustainable source. In addition, it is becoming more expensive.

SUMMARY

In view of the foregoing, it is recognized that a need exists for alternative gels for thermal therapy devices that are well performing, relatively low in cost, and sustainable. The present invention provides therapy devices comprising as the heat transfer member a gel formed with biodiesel by-product glycerin as the antifreeze component of the gel. Such gels have been found to provide surprisingly good performance. Advantageously, they are less expensive than conventional propylene glycol-based gels and are derived from more sustainable sources.

Briefly, the present invention provides a therapy device comprising a flexible sealed envelope and a gel within the envelope. In one embodiment, the gel comprises water, thickening agent, and biodiesel by-product glycerin comprising glycerol (propane-1,2,3-triol) and soap.

In another embodiment, the gel comprises (a) between about 2% and about 5% by weight hydroxypropyl methylcellulose; (b) biodiesel by-product glycerin comprising glycerol and soap; (c) between about 65% and about 73% by weight water; and (d) less than about 0.5% by weight preservative. The glycerol comprises between about 23% and about 25% by weight of said gel and the soap comprises between about 0.01% and about 1% of said gel.

It has been discovered that the above-described biodiesel by-product glycerin gel compositions are well-suited for use in thermal therapy devices for transferring heat from/to an object. The biodiesel by-product glycerin gel compositions remain relatively soft and flexible when cooled to a temperature at least as low as about 0° F. (−18° C.) and yet maintains sufficient viscosity when heated to temperatures up to about 212° F. (100° C.) or higher. In addition, they are made from sustainable materials and are compostable.

DETAILED DESCRIPTION

Biodiesel is produced using a transesterification process. In the transesterification process, oils and/or fats rich in triglycerides are mixed with an alcohol such as methanol or ethanol and a base such as potassium or sodium hydroxide, resulting in a methyl ester biodiesel stream and a glycerin side stream. This glycerin side stream typically contains a mixture of glycerol, methanol (or ethanol), water, inorganic salts (catalyst residue such as NaCl or KCl), free base (for example, NaOH or KOH), free fatty acids, free fats (for example, unreacted mono-, di-, and triglycerides from vegetable oil or animal fat), saponified fat, and a variety of other matter organic non-glycerol (MONG) in varying quantities. As used herein, with reference to biodiesel by-product glycerin, the term "soap" is used to collectively refer to the inorganic salts, free base, free fatty acids, free fats, saponified fat, and MONG within the glycerin side stream. Untreated glycerin side stream typically contains from about 60% to about 80% by weight glycerol, from about 10% to about 20% by weight methanol, and about 12% to about 20% by weight soap and water. Untreated glycerin side stream composition can vary greatly depending upon how efficiently the transesterification process is carried out.

Typically, biodiesel producers strip off the methanol (or ethanol) from the glycerin side stream to reuse it, leaving behind, after neutralization, what is generally known as crude glycerin. In raw form, this crude glycerin can have high salt soap content and substantial color (for example, yellow to dark brown); however, the amount of glycerol, methanol (or ethanol), soap, water and MONG, as well as the pH and color, can vary greatly amongst crude glycerin producers/suppliers. Consequently, crude glycerin has few direct uses due to the presence of the salts and other species, and its fuel value is also marginal. The biodiesel industry generates millions of gallons of crude glycerin waste each year, and the amount produced is growing rapidly along with the dramatic growth of biodiesel production. It has been discovered that such crude glycerin (also referred to herein as "biodiesel by-product glycerin") is well suited for use as a heat sink material in therapy devices. Surprisingly, the presence methanol (or ethanol), soap, and other MONG does not negatively affect the performance of the gel.

Gel compositions useful in the present invention comprise biodiesel by-product glycerin. The gel composition typically comprises between about 25% and about 35% by weight biodiesel by-product glycerin.

The biodiesel by-product glycerin comprises glycerol and soap. The biodiesel by-product glycerin typically comprises between about 60% and about 99.7% by weight glycerol; more typically between about 70% and about 90% by weight glycerol. Food grade biodiesel by-product glycerin, for example, comprises at least 99.7% by weight glycerol. Food grade glycerin is useful in the gel compositions of the invention, but such high purity is not necessary.

The gel compositions of the invention typically comprise between about 15% and about 35% by weight glycerol; preferably, between about 20% and about 30% by weight glycerol; more preferably, between about 23% and about 25% by weight glycerol.

The gel compositions of the invention preferably comprise between about 0.01% and about 1% by weight soap. It has been found that a small amount of soap makes the gel compositions of the invention easier to clean should they be spilled. The soap can include inorganic salts, free base, free fatty acids, saponified fat, free fat, and/or other MONG.

Methanol (or ethanol) is usually stripped from biodiesel by-product glycerin for reuse, but residual methanol is often still present. Preferably, for therapy devices that will be heated (for example, in a microwave), the gel comprises less than about 0.5% alcohol (preferably, less than about 0.1% alcohol).

In addition to biodiesel by-product glycerin, gels useful in the present invention also comprise water and thickening agent. The gel typically comprises between about 50% and about 75% by weight water (preferably, about 65% to about 72% by weight water). The thickening agent can be, for example, a natural gum polymer, a cellulosic, or a cellulose derivative. In each instance, the thickening agent typically comprises about 2% to about 5% by weight of the gel composition. Useful thickening agents include, for example, guar gum, gum tragacanth, locust bean gum, xanthan gum, hydroxypropyl methylcellulose, sodium carboxy methylcellulose, Liporamnosan Brand Polyethylene Glycol (12) Glucopiranose Copolymer, Idroramnosan Brand Polyethylene Glycol (8) Glucopiranose Copolymer, hydroxyethyl cellulose, SGP Brand Absorbent Polymer, and the like.

Hydroxypropyl methylcellulose is a preferred thickening agent. It is generally available in a finely divided, particulate form. A suitable hydroxypropyl methylcellulose is available from Dow Chemical Company, Midland, is type K15M. It is available from Dow Chemical Company under the trademark "METHOCEL".

Sodium carboxy methylcellulose is available S&G Resources, Inc., Medfield, Mass.

Liporamnosan Brand Polyethylene Glycol (12) Glucopiranose Copolymer and Idroramnosan Brand Polyethylene Glycol (8) Glucopiranose Copolymer are available from Tri-K Industries. SGP Brand Absorbent Polymer is a hydrolyzed starch-polyacrylonitrile graft copolymer available from Grain Processing Corporation, Muscatine, Iowa.

Preferably, the pH of the gel compositions of the invention is between about 3 and about 9.

In some embodiments of the invention, the gel further comprises a preservative to inhibit microbial growth. It has been found that the biodiesel by-product glycerin gel can be susceptible to biological contaminants such as bacteria or fungi. The preservative is typically comprises less than about 0.5% by weight of the gel composition. Preservative is typically not necessary, however, if the gel has a relatively high concentration of methanol (for example, more than about 1.5% by weight) and high pH (for example, above about pH 9). Examples of useful preservatives include sodium benzoate and citric acid, parabens (for example, methyl and propyl hydroxybenzoates), formaldehyde, Dowicil™ 200 (available from Dow Chemical Company, Midland, Mich.), and the like. Preferably, the preservative is sodium benzoate and citric acid.

Other adjuvants such as dyes (for example, food grade dyes), may also be added to the gel in trace amounts.

The gel compositions of the invention can be made in large batches (for example, 450 kg to 900 kg batches), by first mixing the thickening agent into the biodiesel by-product glycerin, for example, in drum and mixing it until a uniformly wetted slurry is formed. The slurry can then be dissolved in a tank of water using agitation. If preservatives and/or other adjuvants are being used, they are typically added to the water before the slurry. For example, when sodium benzoate and citric acid are used as preservative, the sodium benzoate is first dissolved into the water and then the citric acid is added and dissolved in the water. Finally, the slurry is added and thoroughly mixed. The biodiesel by-product gel of the present maintains its gel-like consistency over a wide temperature range. For use as a therapy device, it is important that the device/gel remain flexible and conformable, for example, over a range of temperatures from about −18° C. to about 65° C. The gel compositions of the invention remain pliable and conformable (for example, they readily bend and mold to treat various body joints) over this temperature range. When it is to be used as a cold therapy pack, the therapy device of the invention can be stored in the freezer. The therapy devices/gels of the invention remain flexible and conformable upon removal from a typical residential freezer. At temperatures from about −10° C. to about −6° C., for example, the gel compositions of the invention typically comprise less than about 25% ice (preferably, less than about 10% ice). In addition, at temperatures from about −10° C. to about −6° C., the gel compositions of the invention typically contain no ice chunks larger than about 2 $cm^3$ (preferably, no larger than 0.5 $cm^3$; more preferably, no larger than about 0.01 $cm^3$).

The biodiesel by-product gel is sealed in a flexible envelope. The envelope will typically be rectangular, but it may be any shape. For example, in some embodiments the therapy device may be specially configured to facilitate use on particular locations on the body.

The envelope should be a tough material that is liquid impervious and remains pliable and intact over the operating temperature range, for example, from freezer range temperatures when used as a cold pack up to elevated temperatures when used as a heat pack. The envelope is preferably puncture resistant and may be substantially transparent or opaque as desired. Many suitable envelope materials used in currently known therapy devices may be used with devices of the invention. The envelope can be prepared, for example, from polyethylene, polyester, polypropylene, cellulose esters, cellulose ethers, nylon, polyvinyl alcohol acetals, polyvinyl chloride acetate, polystyral, methyl methacrylate, and the like. A preferred bag material is constructed of laminate materials that are microwaveable, such as the polyethylene/nylon or nylon sclair laminate disclosed in U.S. Pat. No. 4,756,311 (Francis). One suitable bag material is 0.0254 mm biaxially oriented nylon laminated to 0.0635 mm polyethylene, which is commonly available for food packaging. Most preferably, the envelope is constructed from a linear low density polyethylene/polyester laminate, such as Scotchpak™ Film, which is a 0.0254 mm polyester/0.0635 mm polyethylene laminate commercially available from 3M Company, St. Paul, Minn. Two sheets of Scotchpak film can be peripherally sealed to each other by a mechanically strong heat seal.

The envelope can be formed and sealed around a forming mandrel, and the gel can be pumped into the envelope as the envelope is formed. The top seal of a filled envelope can be made at the same time, for example, as the bottom seal for the next envelope is made.

In use, the therapy device of the invention can be put into a freezer or other chilling device for use as a cold compress, or can be put into hot water or heated in a microwave to be used as a hot compress. For applying to the human body, the device would typically be heated to about 60° C. and would have the effect of raising the skin temperature of the body (from its normal temperature of about 30° C.) to a level somewhere in the range of from about 35° C. to about 45° C. for a period of at least 20 minutes. The device can be placed in a cloth sleeve, or a bag or pouch such as those described in U.S. Pat. No. 4,953,550 (Dunshee) to moderate the heat so that it the device is not painfully hot against the skin. When used to remove heat from the human body, the device would be cooled to at least about −10° C. (preferably to about −18° C.) and would have the effect of lowering the skin temperature of the body to a level in the range from about 10° C. to about 15° C. for a period of at least 20 minutes.

The therapy device of the invention may be used repeatedly. If, however, the envelope was to become ruptured or the user should simply wish to dispose of it, the biodiesel by-product gel may be composted, as it is biodegradable.

The biodiesel by-product thermal gels of the invention are also useful in other applications such as, for example, providing thermal protection for perishable or temperature-sensitive items during transit or storage. Packs containing the thermal gels of the invention can be used, for example, for keeping food or temperature-sensitive medical supplies cool. They are well-suited for food and medical applications because they are non-toxic; however, they are useful in a variety of other cooling applications as well.

EXAMPLES

The invention will be further explained by the following illustrative examples. The particular materials and amounts thereof recited in these examples, as well as other conditions and details, should not be construed to unduly limit this invention.

Unless otherwise indicated, all amounts are expressed in parts or percent by weight.

Example 1

Gel Composition:
- 30% (90 grams) of Crude Glycerin (Apple Valley Biodiesel Group, Chetek, Wis.)
- 4% (12 grams) Hydroxypropylmethylcellulose—Methocel™ K15M (www.colorcon.com, manufactured by Dow Chemical Company, Midland, Mich.)
- 65.75% (197.25 grams) water
- 0.08% (0.24 grams) sodium benzoate (Emerald Performance Materials, Kalama, Wash.)
- 0.17% (0.51 grams) citric acid (DeWolf Chemical Company, East Providence, R.I.)

Into a 1 quart size plastic zipper closure storage bag was placed 90 grams of warmed biodiesel byproduct glycerin obtained from Apple Valley Biodiesel Group. The Apple Valley Biodiesel Byproduct Glycerin was a semisolid at room temperature and had to be warmed slightly to be in liquid form. To the glycerin byproduct was added 12 grams of Methocel™ K15M powder hydroxypropylmethylcellulose and mixed with finger kneading of the bag to form a uniformly wetted syrup of the glycerin and powder. 197.25 grams of water was measured into a separate container and 0.24 grams of sodium benzoate NF powder, obtained from Emerald Performance Materials, was dissolved into the water. Into the resulting water and sodium benzoate solution 0.51 grams of Jungbunzlauer citric acid obtained from DeWolf Chemical Company, was then dissolved. The resulting water and preservative mixture was then added to the glycerin/Methocel™ slurry. The bag was zipped closed taking care to get most or all of the air from the bag. When the bag was completely closed, the mixture was shaken vigorously and kneaded to get all ingredients uniformly mixed. A thick gel formed in about a minute. The bag was placed on a flat surface. It took several hours for the Methocel™ to completely hydrate and become a translucent gel. This gel was firm because of the soap content in the glycerin byproduct. The analysis on this crude glycerin was done by NMR and found to be:

71.41% Glycerol 11.28% Methanol 17.31% Soap

This gel was very firm at room temperature but very flexible and free of large ice crystal structures that cause a harsh tactile feel to the gel when frozen to −9° C. to −6° C.

Example 2

Gel Composition:
- 30% (90 grams) of Glenn Crude Glycerin (Glenn Corporation, White Bear Lake, Minn.)
- 4% (12 grams) Hydroxypropylmethylcellulose—Methocel™ K15M
- 65.75% (197.25) grams water
- 0.08% (0.24 grams) sodium benzoate
- 0.17% (0.51) grams citric acid Into a 1 quart size plastic zipper closure storage bag was placed 90 grams of biodiesel byproduct glycerin obtained from Glenn Corporation. The Glen Corporation Biodiesel Byproduct Glycerin was a viscous liquid at room temperature. To the glycerin byproduct was added 12 grams of Methocel™ K15M powder hydroxypropylmethylcellulose and mixed with finger kneading of the bag to form a uniformly wetted syrup of the glycerin and powder. 197.25 grams of water was measured into a separate container and 0.24 grams of sodium benzoate NF powder was dissolved into the water. Into the resulting water and sodium benzoate solution 0.51 grams of Jungbunzlauer citric acid was then dissolved. The resulting water and preservative mixture was then added to the glycerin/Methocel™ slurry. The bag was zipped closed taking care to get most or all of the air from the bag. When the bag was completely closed, the mixture was shaken vigorously and kneaded to get all ingredients uniformly mixed. A thick gel formed in about a minute. The bag was placed on a flat surface. It took several hours for the Methocel™ to completely hydrate and become a translucent gel. The analysis on this Glenn crude glycerin was done by NMR and found to be:

89.8% Glycerin 1.65% Methanol 1.85% Water 6.48% soap and ash 0.22% sodium chloride

Example 3

Gel Composition:
- 30% (90 grams) of Glenn Crude Glycerin (Glenn Corporation, White Bear Lake, Minn.)
- 4% (12 grams) Sodium carboxy methylcellulose (S&G Resources, Inc., Medfield, Mass.)
- 65.75% (197.25) grams water
- 0.08% (0.24 grams) sodium benzoate
- 0.17% (0.51) grams citric acid Into a 1 quart size plastic zipper closure storage bag was placed 90 grams of biodiesel byproduct glycerin obtained from Glenn Corporation. The Glen Corporation Biodiesel Byproduct Glycerin was a viscous liquid at room temperature. To the glycerin byproduct was added 12 grams of sodium carboxy methylcellulose powder and mixed with finger kneading of the bag to form a uniformly wetted syrup of the glycerin and powder. 197.25 grams of water was measured into a separate container and 0.24 grams of sodium benzoate NF powder was dissolved into the water. Into the resulting water and sodium benzoate solution 0.51 grams of Jungbunzlauer citric acid was then dissolved. The resulting water and preservative mixture was then added to the glycerin/sodium carboxy methylcellulose slurry. The bag was zipped closed taking care to get most or all of the air from the bag. When the bag was completely closed, the mixture was shaken vigorously and kneaded to get all ingredients uniformly mixed. A thick gel formed in about a minute. The bag was placed on a flat surface. It took several hours for the sodium carboxy methylcellulose to completely hydrate and become a translucent gel. The analysis on this Glenn crude glycerin was done by NMR and found to be:
- 89.8% Glycerin
- 1.65% Methanol
- 1.85% Water
- 6.48% soap and ash
- 0.22% sodium chloride

Example 4

Gel Composition:
- 25% (75 grams) of Glenn USP Kosher Biodiesel Glycerin (Glenn Corporation, White Bear Lake, Minn.)
- 4% (12 grams) Hydroxypropylmethylcellulose—Methocel™ K15M
- 70.75% (212.25) grams water
- 0.08% (0.24 grams) sodium benzoate
- 0.17% (0.51) grams citric acid Into a 1 quart size plastic zipper closure storage bag was placed 75 grams of kosher biodiesel byproduct glycerin obtained from Glenn Corporation. The Glen Corporation Biodiesel Byproduct Kosher Glycerin was a viscous liquid at room temperature. To the kosher glycerin byproduct was added 12 grams of Methocel™ K15M powder hydroxypropylmethylcellulose and mixed with finger kneading of the bag to form a uniformly wetted syrup of the glycerin and powder. 212.25 grams of water was measured into a separate container and 0.24 grams of sodium benzoate NF powder was dissolved into the water. Into the resulting water and sodium benzoate solution 0.51 grams of Jungbunzlauer citric acid was then dissolved. The resulting water and preservative mixture was then added to the glycerin/Methocel™ slurry. The bag was zipped closed taking care to get most or all of the air from the bag. When the bag was completely closed, the mixture was shaken vigorously and kneaded to get all ingredients uniformly mixed. A thick gel formed in about a minute. The bag was placed on a flat surface. It took several hours for the Methocel™ to completely hydrate and become a translucent gel. The analysis on this Glenn kosher glycerin is:
- 99.7% Glycerol
- 0.5% Methanol, water and soap

What is claimed is:

1. A therapy device comprising a flexible sealed envelope and a gel within said envelope, said gel comprising water, thickening agent, and biodiesel by-product glycerin comprising glycerol and soap.

2. The therapy device of claim 1 wherein said biodiesel by-product glycerin further comprises an alcohol selected from the group consisting of methanol and ethanol.

3. The therapy device of claim 2 wherein said alcohol is methanol.

4. The therapy device of claim 2 wherein said gel comprises less than about 0.5% by weight alcohol.

5. The therapy device of claim 1 wherein said gel comprises between about 15% and about 35% by weight glycerol.

6. The therapy device of claim 5 wherein said gel comprises between about 20% and about 30% by weight glycerol.

7. The therapy device of claim 6 wherein said gel comprises between about 23% and about 25% by weight glycerol.

8. The therapy device of claim 1 wherein said soap comprises free fatty acids, and mono-, di- and tri-glycerides.

9. The therapy device of claim 1 wherein said thickening agent is a natural gum polymer, a cellulosic, or a cellulose derivative.

10. The therapy device of claim 9 wherein said thickening agent is hydroxypropyl methylcellulose.

11. The therapy device of claim 1 wherein said gel further comprises preservative.

12. The therapy device of claim 11 wherein said preservative comprises sodium benzoate and citric acid.

13. The therapy device of claim 1 wherein said gel has a pH between about 3 and about 9.

14. The therapy device of claim 1 wherein said gel is conformable at temperatures from about −10° C. to about −6° C.

15. The therapy device claim 1 wherein said gel contains no ice chunks larger than about 2 cm$^3$ at temperatures from about −10° C. to about −6° C.

16. The therapy device of claim 15 wherein said gel contains no ice chunks larger than about 0.5 cm$^3$ at temperatures from about −10° C. to about −6° C.

17. The therapy device of claim 16 wherein said gel contains no ice chunks larger than about 0.01 cm$^3$ at temperatures from about −10° C. to about −6° C.

18. A therapy device comprising a flexible sealed envelope and a gel within said envelope, said gel comprising:
 (a) between about 2% and about 5% by weight hydroxypropyl methyl cellulose;
 (b) biodiesel by-product glycerin comprising glycerol and soap;
 (c) between about 65% and about 73% by weight water; and
 (d) less than about 0.5% by weight preservative;
wherein said glycerol accounts for between about 23% and about 25% by weight of said gel and said soap accounts for between about 0.01% and about 1% by weight of said gel.

19. The therapy device of claim 18 wherein said biodiesel by-product glycerin comprises methanol, said methanol being present in said gel in an amount less than about 0.5% by weight.

20. A thermal gel comprising water, thickening agent, and biodiesel by-product glycerin comprising glycerol and soap.

21. The thermal gel of claim 20 further comprises methanol or ethanol.

* * * * *